United States Patent [19]

Nishiki

[11] Patent Number: 5,027,380
[45] Date of Patent: Jun. 25, 1991

[54] DIAGNOSTIC X-RAY APPARATUS
[75] Inventor: Masayuki Nishiki, Ootawara, Japan
[73] Assignee: Kabushiki Kaisha Toshiba, Kawasaki, Japan
[21] Appl. No.: 422,661
[22] Filed: Oct. 17, 1989
[30] Foreign Application Priority Data
Oct. 24, 1988 [JP] Japan .................. 63-267497
[51] Int. Cl.$^5$ .................. H05G 1/64; A61B 1/00; H04N 5/32
[52] U.S. Cl. .................. 378/4; 378/99; 378/98; 378/62; 358/111
[58] Field of Search .................. 378/4, 6, 10, 16, 21, 378/19, 148, 165–166, 99, 98, 116; 250/370.09; 358/111

[56] References Cited
U.S. PATENT DOCUMENTS

| 4,433,429 | 2/1984 | Finkenzeller et al. | 378/165 |
| 4,733,313 | 3/1988 | Izumita et al. | 358/111 |
| 4,884,291 | 11/1989 | Nicolay | 378/99 |

FOREIGN PATENT DOCUMENTS

| 0105618 | 4/1984 | European Pat. Off. | 378/86 |
| 117524 | 5/1984 | European Pat. Off. | |
| 157417 | 9/1985 | European Pat. Off. | |
| 3121176 | 12/1982 | Netherlands | 378/4 |

OTHER PUBLICATIONS

Gruner; "CCD and Vidicon . . . Practice (invited)"; 1989; pp. 1545–1551.

Primary Examiner—Edward P. Westin
Assistant Examiner—Don Wong
Attorney, Agent, or Firm—Oblon, Spivak, McClelland, Maier & Neustadt

[57] ABSTRACT

In an X-ray fluoroscopic apparatus, a diaphragm is inserted in an X-ray emitted from an X-ray tube onto an object to be examined, and only a desired slice of the object is exposed with X-rays emitted from a large number of directions. The X-ray transmitted through the object is caused to be incident on an image intensifier, and an optical image therefrom is incident on a TV camera formed of a solid-state image pickup device, such as a CCD, through an optical system. An output from the TV camera is supplied to a memory, X-ray projection data from a large number of directions are stored in the memory, and an output from the memory is supplied to an image reconstruction processor, thus reconstructing a tomogram. The optical image from the image intensifier is incident on only one or a plurality of horizontal scanning lines corresponding to the slice in an imaging area of the TV camera. Therefore, pixel data in a region except for the region corresponding to the slice are vertically transferred at high speed, are accumulated in a horizontal transfer CCD, are output from the horizontal transfer CCD, and are discharged without being written in the memory. The pixel data of the slice are vertically transferred at normal speed, are output from the horizontal transfer CCD line by line, and are written in the memory.

11 Claims, 4 Drawing Sheets

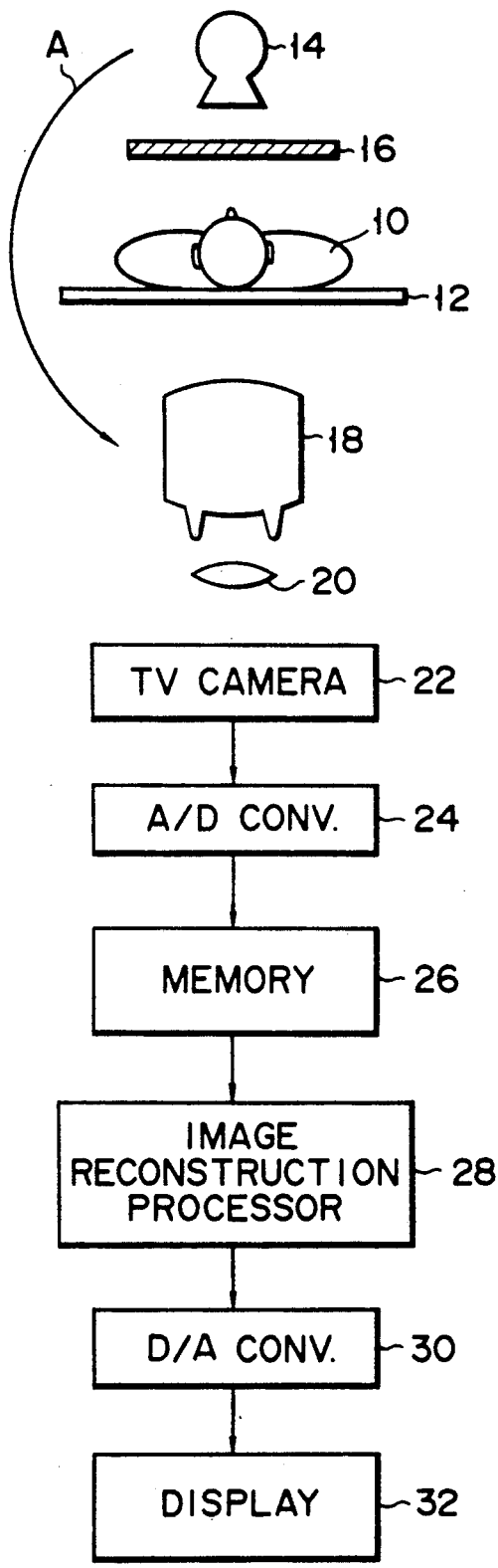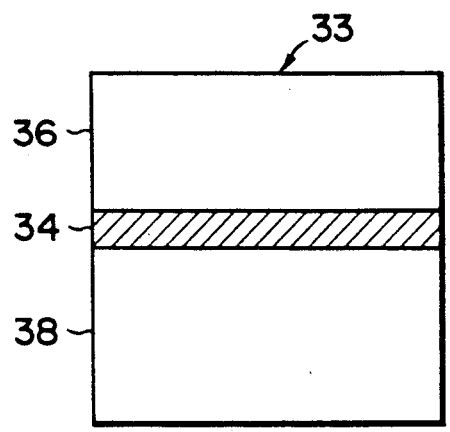
FIG. 1 (PRIOR ART)
FIG. 2 (PRIOR ART)

DIAGNOSTIC X-RAY APPARATUS

BACKGROUND OF THE INVENTION

1. Field of the Invention

The present invention relates to a diagnostic X-ray apparatus which can obtain a fluorogram and a tomogram (CT image).

2. Description of the Related Art

Conventionally, simulation for a treatment program is performed in order to determine an amount of X-ray emission, a direction of X-ray emission, and the like prior to X-ray diagnosis and X-ray treatment. For the purpose of this simulation, a tomogram is often obtained in addition to a fluorogram. However, since a conventional X-ray fluoroscopic apparatus can obtain only a fluorogram, a tomogram must be obtained using another CT apparatus. This operation is complicated and timeconsuming. In addition, when a patient is exposed with X-rays twice, the health of the patient may be adversely affected. Therefore, a demand has arisen for developing an X-ray diagnostic apparatus which can obtain a tomogram in addition to a fluorogram.

FIG. 1 shows an arrangement of a diagnostic X-ray apparatus which is constructed by additionally providing a function for obtaining a tomogram on the basis of the conventional X-ray fluoroscopic apparatus. The X-ray apparatus in FIG. 1 has been developed in accordance with the above-mentioned demand. X-ray beam emitted from an X-ray tube 14 is emitted onto one slice of an object 10 to be examined on a bed 12 through a diaphragm 16 for defining the slice having a predetermined thickness. The diaphragm 16 has a rectangular aperture perpendicular to the axis of the object 10. The slice of the object 10 is exposed with fan X-ray emitted from the diaphragm 16. When a fluorogram is obtained, the diaphragm 16 is removed. A case wherein a tomogram is obtained will be described hereinafter. The X-ray transmitted through one slice of the object 10 is incident on an image intensifier 18. The transmitted X-ray representing the degree of X-ray absorbance of tissues in the slice is converted into a light beam, and is output. The light beam is incident on a TV camera 22 through an optical system 20, and is converted into an analog signal, thus obtaining a projection signal representing the degree of X-ray absorbance of tissues in the slice. The X-ray tube 14, the diaphragm 16, the image intensifier 18, the optical system 20, and the TV camera 22 are aligned along a line, and can be integrally rotated in a direction indicated by an arrow A in FIG. 1 with respect to the object 10 in order to obtain a tomogram. In addition, in order to obtain a fluorogram from an arbitrary direction, the above units can be arranged to face any direction with respect to the object 10.

The analog projection signal output from the TV camera 22 is converted into a digital signal by an A/D converter 24, thus obtaining X-ray projection data. While the X-ray tube 14 and the like are rotated once in the direction indicated by the arrow A in FIG. 1 around the object 10, an X-ray is emitted for each predetermined angle, and X-ray projection data at each angle is written in a memory 26. The projection data read out from the memory 26 is supplied to an image reconstruction processor 28, and a tomogram of the slice is reconstructed. The obtained tomogram is input to a display 32 through a D/A converter 30, and is displayed.

The X-ray apparatus with the above arrangement can acquire X-ray projection data in the same manner as in the conventional CT apparatus by emitting an X-ray onto one slice of the object through the diaphragm 16, and by using the image intensifier 18 and the TV camera 22 as X-ray detectors. When a fluorogram is obtained, the diaphragm 16 may be removed to emit X-ray onto a given area of the object, and an output from the TV camera 22 or the memory 26 may be displayed or recorded.

Such an X-ray apparatus, however, has the following problems. A screen of the image intensifier 18 has a circular shape and an imaging area of the TV camera 22 has a square shape in order to obtain a fluorogram. When a tomogram is obtained, however, an X-ray is emitted onto a slice of the object 10 through the diaphragm 16. Therefore, as shown in FIG. 2, a light beam from the image intensifier 18 is only incident on a strip region 34 of an imaging area 33 of the TV camera 22. The strip region 34 corresponds to the slice. For this reason, when the TV camera 22 normally performs a scanning operation, i.e., the entire imaging area 33 (regions 36, 34, and 38) is scanned, the regions 36 and 38 which receive no light beams are unnecessarily scanned. This operation is a waste of time. Therefore, when a tomogram is obtained, a time period required for acquiring projection data is unnecessarily prolonged. As a result, a time for obtaining a tomogram is undesirably prolonged. In addition, since unnecessary data read out from the regions 36 and 38 are written in the memory 26, the memory 26 cannot be effectively used.

SUMMARY OF THE INVENTION

It is an object of the present invention to provide a diagnostic X-ray apparatus which can acquire projection data for obtaining a tomogram in a short period of time.

It is another object of the present invention to provide an X-ray fluoroscopic apparatus comprising an image intensifier and a TV camera formed of a solid-state image pickup device, wherein, in a tomography mode, only necessary data in a part of the imaging area, on which a light beam is incident from the image intensifier, is read out from the solid-state image pickup device at high speed, the readout data is written in a memory to reconstruct a tomogram, a time period required for acquiring data is shortened, and the memory is effectively used.

According to the present invention, there is provided an X-ray apparatus comprising an X-ray source for emitting an X-ray from a large number of directions onto one slice of an object, an image intensifier for converting the X-ray transmitted through the object to a light beam, a solid-state image pickup device for sensing the light beam output from the image intensifier, a controller for reading only image data corresponding to the slice from the solid-state image pickup device, and an image reconstruction processor for obtaining a tomogram of the slice on the basis of the readout image data.

According to such an X-ray apparatus, all data in the imaging area of the solid-state image pickup device are not read out, but only X-ray projection data in a region of the imaging area, which receives a light beam from the image intensifier and corresponds to the slice, is optimally read out, so that a time period required for acquiring data can be greatly shortened, and the memory for storing the acquired data can be effectively used.

BRIEF DESCRIPTION OF THE DRAWINGS

FIG. 1 is a schematic block diagram showing an arrangement of a conventional diagnostic X-ray apparatus;

FIG. 2 is a view showing an imaging area of a TV camera in the apparatus shown in FIG. 1;

DETAILED DESCRIPTION OF THE PREFERRED EMBODIMENT

Figure 3:
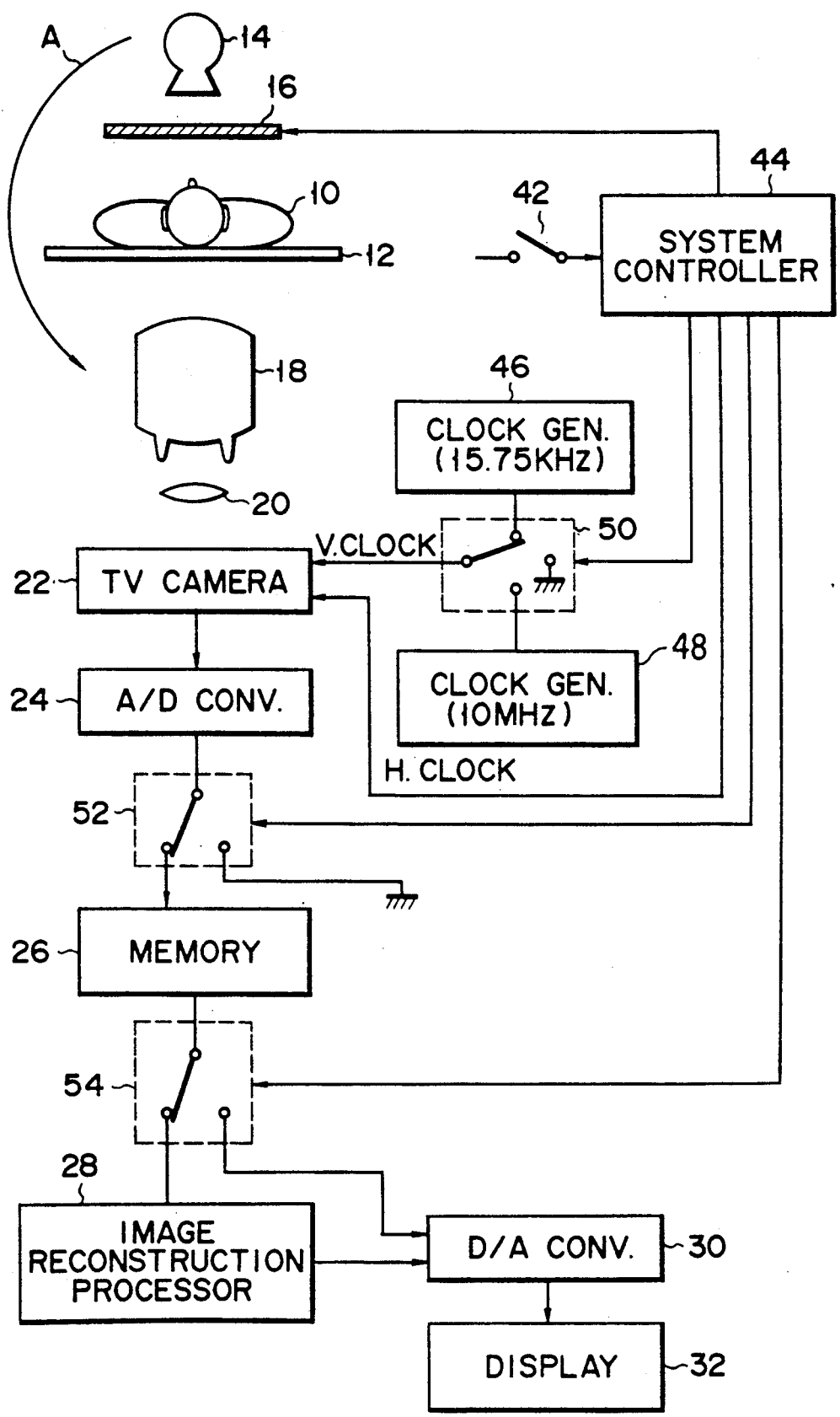
FIG. 3 is a block diagram of a diagnostic X-ray apparatus according to an embodiment of the present invention.

A diagnostic X-ray apparatus according to an embodiment of the present invention will be described hereinafter with reference to the accompanying drawings. FIG. 3 is a block diagram showing an arrangement of the embodiment. The same reference numerals in FIG. 3 denote the corresponding parts as in FIG. 1. A diaphragm 16 has a motor (not shown). Using the motor, the position and width of an aperture of the diaphragm can be changed. In a fluorography mode, the width of the aperture is increased to correspond the entire surface of a screen, to which an X-ray is incident, of an image intensifier 18. In a tomography mode, the size of the aperture is decreased so that its position and width correspond to a desired slice of an object 10 to be examined. For the purpose of this control operation, a control signal is supplied from a system controller 44 to the diaphragm 16. A mode designation switch 42 is connected to the system controller 44 to select an operation mode, i.e., tomography or fluorography mode. The structure in which the X-ray transmitted through an object 10 is incident on a TV camera 22 through an image intensifier 18 and an optical system 20 is the same as in the apparatus shown in FIG. 1.

Figure 4:
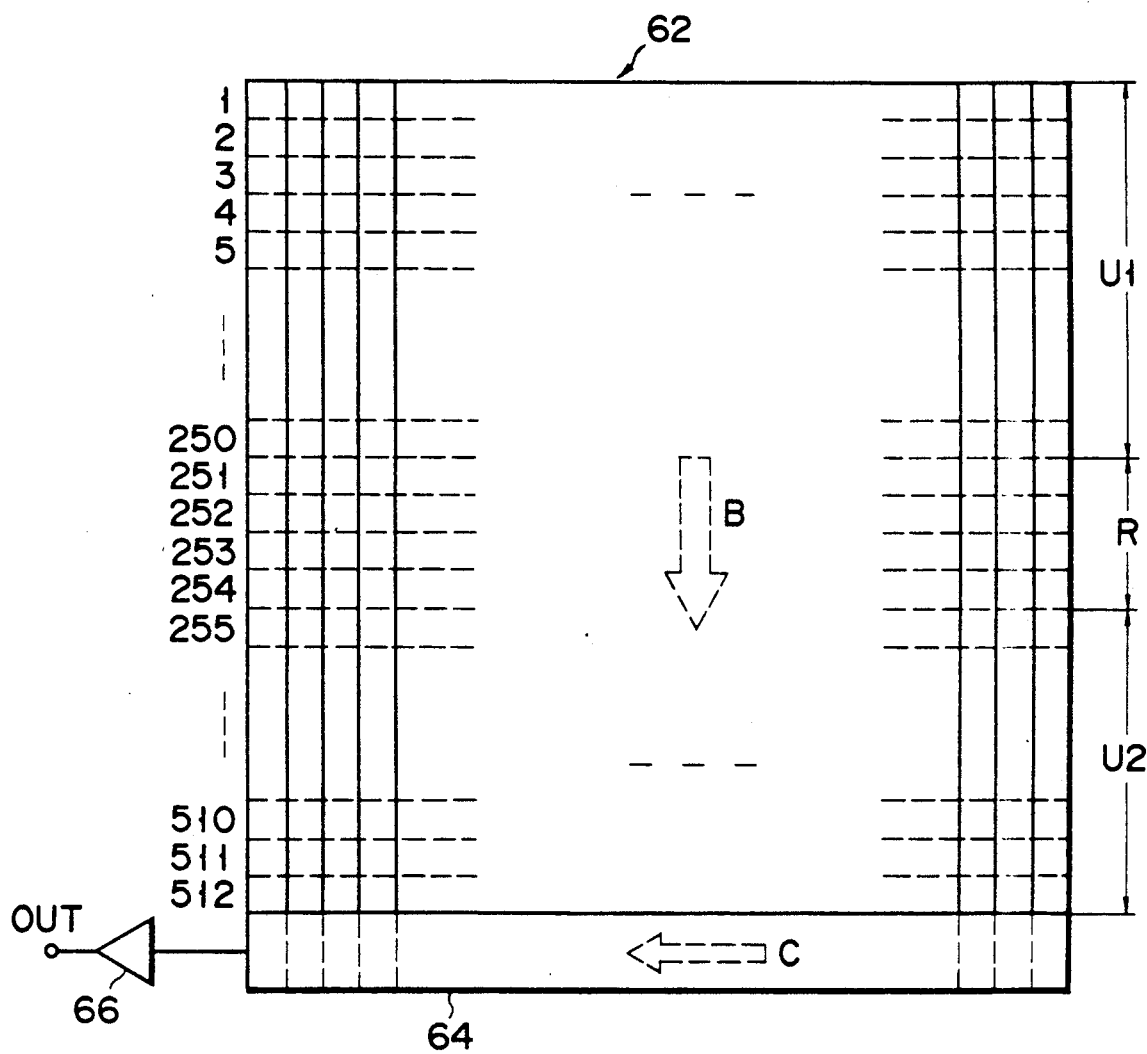
FIG. 4 is a view showing a tow-dimensional structure of CCD used in a TV camera in the embodiment.

The TV camera 22 is formed of solid-state image pickup device such as a CCD. An arrangement of the CCD is shown in FIG. 4. Although an interline transfer system CCD is employed as the solid-state image pickup device in FIG. 4, CCD of the other systems such as frame transfer system CCD may be employed. A large number of vertical transfer CCDs 62 are arranged on the imaging area of the TV camera 22. Each CCD 62 is divided into 512 lines (512 pixels), and data of the pixels are transferred line by line in the vertical direction indicated by an arrow B in synchronism with a vertical transfer clock. One horizontal transfer CCD 64 is arranged at the lower end of all the vertical transfer CCDs 62. The CCD 64 transfers pixel data of a line transferred from all the vertical transfer CCDs 62 pixel by pixel in the horizontal direction indicated by an arrow C in synchronism with a horizontal transfer clock. The data output from the CCD 64 is output through a buffer 66, and is supplied to an A/D converter 24.

In this embodiment, the TV camera 22 requires two types of vertical transfer clock signals. Therefore, a first clock generator 46 having a normal frequency (in this case, a frequency of a horizontal synchronizing signal of a TV signal of an NTSC system: 15.75 kHz), and a second clock generator 48 having a frequency (e.g., 10 MHz) higher than the normal frequency, are provided. The first and second clock signals from the generators 46 and 48 are supplied to the TV camera 22 through a selector 50. A selection operation of the selector 50 is controlled by the system controller 44. The selector 50 includes first and second terminals respectively connected to the first and second clock generators 46 and 48, and a third terminal which is grounded. The third terminal is used to interrupt a vertical transfer operation. The horizontal transfer clock signal is directly supplied from the system controller 44 to the TV camera 22, and its frequency is always kept constant.

An output from the A/D converter 24 is supplied to a selector 52. The selector 52 includes a first terminal connected to a memory 26, and a second terminal which is grounded. A selection operation of the selector 52 is also controlled by the system controller 44. When pixel data which have been vertically transferred in response to the first vertical transfer clock signal are output from the A/D converter 24, the selector 52 is switched to the first terminal side to write the readout data in the memory 26. When pixel data which have been vertically transferred in response to the second vertical transfer clock signal are read out from the A/D converter 24, the selector 52 is switched to the second terminal side to discharge the readout data through the ground terminal. Therefore, non-effective use of the memory 26, caused by storage of unnecessary data, can be prevented. Note that X-ray projection data from a large number of directions acquired upon one rotation of an X-ray tube 14 around the object 10 are stored in the memory 26.

An output from the memory 26 is input to a selector 54. The selector 54 includes a first terminal connected to an image reconstruction processor 28, and a second terminal connected to a D/A converter 30. The selector 54 is switched by the system controller 44 to supply an output from the memory 26 to the image reconstruction processor 28 in a tomography mode, and to directly supply the output from the memory 26 to the D/A converter 30 in a fluorography mode. Note that, in the fluorography mode, an output from the TV camera 22 may be directly supplied to a display 32, and may be displayed thereby.

An operation of this embodiment will be described hereinafter. First, an operation in the tomography mode will be described below. In this mode, the system controller 44 supplies a control signal to the diaphragm 16, and the width of the aperture of the diaphragm 16 is decreased to a predetermined width at a predetermined position corresponding to a slice of the object. In addition, the selector 54 is connected to the first terminal side, and the output from the memory 26 is input to the image reconstruction processor 28, thus reconstructing the tomogram. The X-ray tube 14, the diaphragm 16, the image intensifier 18, the optical system 20, and the TV camera 22 are integrally rotated around the object 10 in a direction indicated by an arrow A in FIG. 3 by each predetermined angle, and projection data is acquired at each angle as follows. The system controller 44 internally generates a frame synchronizing signal, and controls the selector 50 in synchronism with the frame synchronizing signal and in accordance with the position and width of the aperture of the diaphragm 16 to supply the first or second vertical transfer clock signal to the TV camera 22. The system controller 44 also supplies a horizontal transfer clock signal having a constant frequency to the TV camera 22 at a predetermined timing. The system controller 44 also connects the selector 52 to the memory 26 during a predetermined period, and writes the necessary data in the memory 26.

As described above, in the tomography mode, a light beam is not incident on the entire imaging area of the TV camera 22, but the light beam from the image intensifier 18 is incident on only a strip portion, corresponding to a slice of the object, onto which an X-ray limited by the diaphragm 16 is emitted. In this case, assume that a light beam is incident on a region R (region consisting of four horizontal scanning lines, i.e., the 251st to 254th lines) in FIG. 4 corresponding to the slice. A region U1 consisting of the first to 250th horizontal scanning lines, and a region U2 consisting of the 255th to 512th horizontal scanning lines receive no light beams. X-ray projection data to be read out from the TV camera 22 and to be written in the memory 26 exist only in the region R. Pixel data in the regions U1 and U2 need not be written in the memory 26. In this embodiment, therefore, until data to be read out are written in the horizontal transfer CCD 64, the pixel data are vertically transferred at high speed, accumulated in the horizontal transfer CCD 64, integrally read out from the CCD 64, and discharged through the ground terminal through the second terminal of the selector 52 without being written in the memory 26. After the data to be read out are written in the horizontal transfer CCD 64, the data in the horizontal transfer CCD 64 are horizontally transferred, the data are vertically transferred at normal speed, and the data read out from the TV camera 22 are supplied to the memory 26 through the first terminal of the selector 52. Since the vertical transfer is performed at normal speed, the data in the next line are written in the horizontal transfer CCD 64 after the data of each line are output from the horizontal transfer CCD 64. When a write operation of the data in the region R to the memory 26 is completed, high-speed vertical transfer, accumulation of the data in the horizontal transfer CCD 64, a read operation of the accumulated data, and a discharge operation of the readout data to the ground terminal are restarted.

Figure 5:
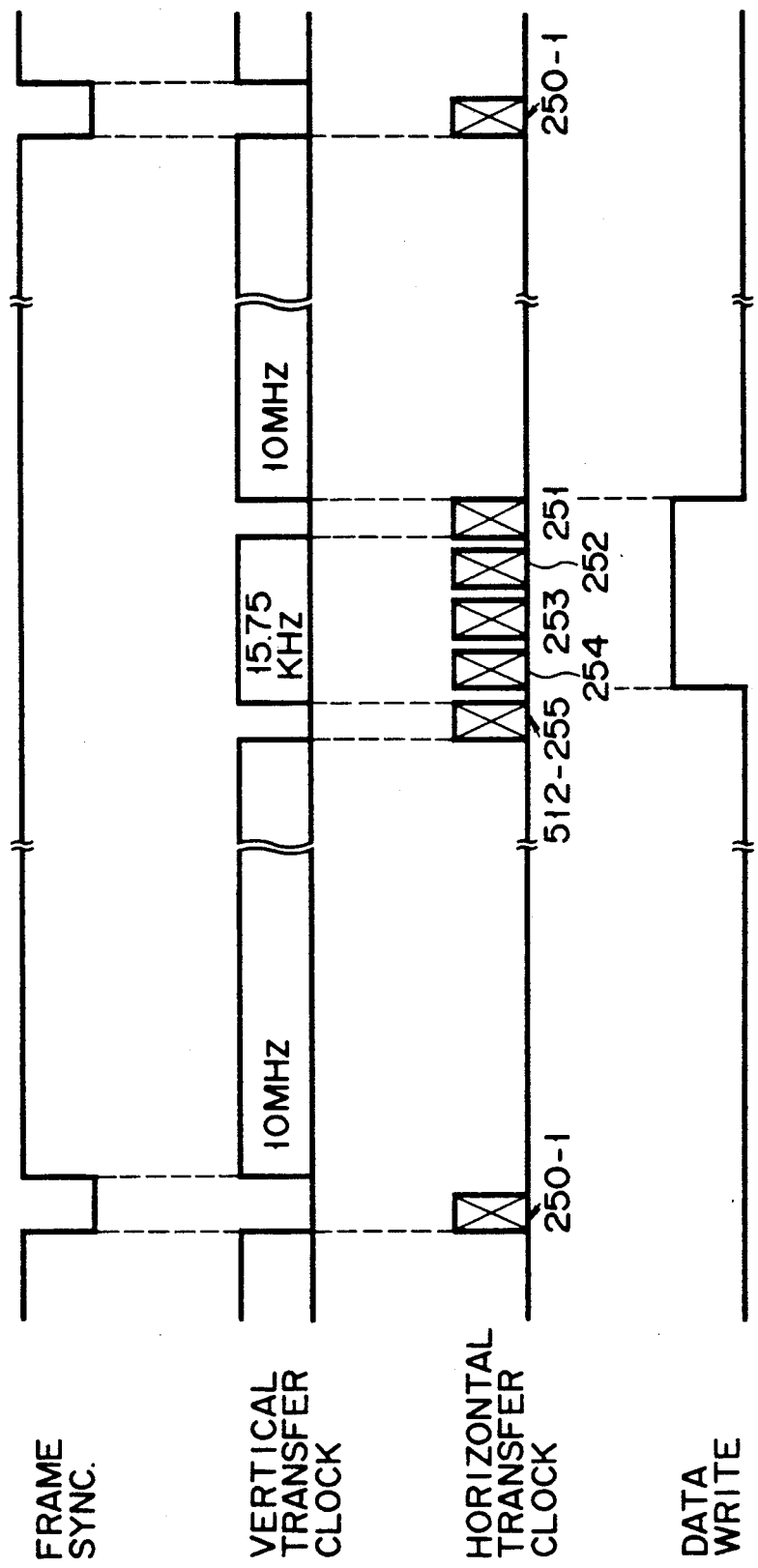
FIG. 5 is a timing chart showing an operation of the CCD.

This operation is shown in the timing chart in FIG. 5. More specifically, when the frame synchronizing signal is rendered active ("H" level), and an imaging period of one frame is started, the system controller 44 connects the selector 50 to the second terminal side, and the second clock signal having a frequency of 10 MHz is supplied to the TV camera 22 as a vertical transfer clock signal. At this time, the horizontal transfer clock is not supplied. Therefore, pixel data of each line is transferred at high speed in the vertical direction indicated by the downward arrow B in FIG. 4. The pixel data of the lines are sequentially transferred line by line from the lowermost 512th horizontal scanning line to the horizontal transfer CCD 64, and are stored or accumulated in the horizontal transfer CCD 64. Unlike in a normal operation, a vertical transfer operation at this time can be performed at very high speed because a horizontal transfer operation for each line transfer is not required. Therefore, a transfer time period of data in the unnecessary region can be shortened. When the pixel data of the uppermost 255th horizontal scanning line in the unnecessary region U2 are transferred to the horizontal transfer CCD 64, the selector 5 is temporarily connected to the third terminal (ground terminal), and supply of the vertical transfer clock is interrupted.

Thereafter, the system controller 44 supplies the horizontal transfer clock to the TV camera 22. The pixel data of the 512th to 255th lines accumulated in the horizontal transfer CCD 64 are horizontally transferred, and are output through the buffer 66. At this time, however, the selector 52 is still connected to the second terminal side, and the readout pixel data are discharged through the ground terminal, i.e., the data is not written in the memory 26.

When this horizontal transfer operation is completed, the selector 50 is switched to the first clock generator 46 side, and the vertical transfer clock signal having a frequency of 15.75 kHz is supplied to the TV camera 22. When the pixel data is vertically transferred by one line, i.e., the pixel data of the lowermost 254th horizontal scanning line in the region R is transferred to the horizontal transfer CCD 64, the horizontal transfer clock signal is supplied, and the pixel data of the 254th line in the horizontal transfer CCD 64 are read out. At this time, the selector 52 is switched to the first terminal side, and these readout data are written in the memory 26. Similarly, vertical and horizontal transfer operations of the pixel data of each line are repeated. When the pixel data of the uppermost 251st horizontal scanning line in the region R is written in the horizontal transfer CCD 64, the selector 50 is switched to the third terminal, and supply of the vertical transfer clock is interrupted.

Thereafter, when the pixel data of the 251st scanning line in the horizontal transfer CCD 64 are horizontally transferred, are output through the buffer 66, and are written in the memory 26, the selector 50 is connected to the second terminal, supply of the high-speed vertical transfer clock signal having a frequency of 10 MHz is restarted, and the selector 52 is switched to the ground terminal side. Note that supply of the horizontal transfer clock signal is interrupted at this time. Therefore, the pixel data of the 250th to first horizontal scanning lines in the unnecessary region U1 are transferred at high speed in the vertical direction indicated by the arrow B, and are accumulated in the horizontal transfer CCD 64. Then, when the imaging period of one frame is completed, and the frame synchronizing signal is rendered nonactive ("L" level), the selector 50 is connected to the third terminal side, and supply of the vertical transfer clock signal is interrupted. The horizontal transfer clock signal is transferred to the TV camera 22, and the pixel data of the 250th to first lines accumulated in the horizontal transfer CCD 64 are output. Also at this time, the selector 52 is connected to the ground terminal, and the readout pixel data are discharged through the ground terminal, i.e., are not written in the memory 26.

Thus, only projection data from a large number of directions of a desired slice of the object defined by the diaphragm 16 are stored in the memory 26.

In the fluorography mode, the width of the aperture of the diaphragm 16 is increased, the selector 50 is always connected to the first clock generator 46 side, and the first clock signal having a frequency of 15.75 kHz is supplied as a vertical transfer clock signal. In addition, the horizontal transfer clock signal is always supplied, pixel data of the entire imaging area of the TV camera 22 is normally read out, the readout data is supplied to the display 32 through the A/D converter 24, the first terminal of the selector 52, the memory 26, the second terminal of the selector 54, and the D/A converter 30, and the data is displayed by the display 32.

As described above, according to this embodiment, there is provided an X-ray fluoroscopic apparatus, wherein an X-ray emitted onto the object is limited by the diaphragm to be incident onto only a desired slice of the object, data in only a region corresponding to the slice is read out from the TV camera 22 using the CCD for picking up an optical image output from the image intensifier 18 which converts the transmitted fluorogram into an optical image, the readout data is stored in the memory 26 to reconstruct the tomogram, and data except for the data corresponding to the slice are output at high speed and are discharged. Therefore, a tomogram can be obtained in a short period of time required for acquiring X-ray projection data, and the memory 26 can be effectively used. Switch timings of the selectors 50 and 52 for controlling a read operation from the TV camera 22, and a write operation to the memory 26 are determined in accordance with the width and position of the aperture of the diaphragm 16 for defining the width and position of the slice. Therefore, the width and position of the slice can be changed. Therefore, the tomogram of the slice having an arbitrary width can be obtained at an arbitrary position of the object only when the arbitrary slice is located within the range of an X-ray incident screen of the image intensifier 18, and hence a degree of freedom of the tomography can be increased.

Note that this invention is not limited to the above embodiments, and various changes and modifications may be made without departing from the spirit and scope of the invention. For example, this apparatus may obtain only a tomogram without a fluorogram. The solid-state image pickup device is not limited to a CCD, but a MOS device can be used.

What is claimed is:

1. An X-ray apparatus comprising:
   an X-ray source for emitting an X-ray onto an object;
   means for setting an operation mode in a first or second operation mode;
   diaphragm means for limiting the X-ray emitted from said X-ray source to emit the X-ray onto a slice of said object, a tomogram of which is to be obtained, in the first operation mode, and not limiting the X-ray to emit the X-ray onto a portion of said object, a fluorogram of which is to be obtained, in the second operation mode;
   an image intensifier for converting an X-ray image transmitted through said object into an optical image;
   solid-state image pickup means for imaging an optical image output from said image intensifier and received in an imaging area to output an image data;
   memory means for storing an output from said solid-state image pickup means; and
   means for reading image data of a region corresponding to said slice in the imaging area from said solid-state image pickup means at a predetermined speed, storing the readout data in said memory means, discharging image data of a region except for said region corresponding to said slice from said solid-state image pickup means at a speed higher than the predetermined speed, without storage in said memory means, in the first operation mode, and for reading image data of the entire imaging area from said solid-state image pickup means at the predetermined speed to store the readout data in said memory means in the second operation mode.

2. The apparatus according to claim 1, further comprising:
   means for integrally rotating said X-ray source, said diaphragm means, said image intensifier, and said solid-state image pickup means around said object to acquire X-ray projection data of said object from a large number of directions in the first operation mode;
   means for reconstructing a tomogram of said slice using the data in said memory means in the first operation mode;
   first display means for displaying the reconstructed tomogram; and
   second display means for displaying a fluorogram based on the data in said memory in the second operation mode.

3. The apparatus according to claim 1, in which said diaphragm means comprises means for changing a degree of X-ray limited in the first operation mode to arbitrarily set the position and thickness of said slice.

4. The apparatus according to claim 3, in which
   said solid-state image pickup means comprises a plurality of vertical transfer CCDs, and a horizontal transfer CCD arranged at one end of the vertical transfer CCDs;
   said diaphragm means comprises means for limiting an X-ray in a vertical direction of said solid-state image pickup means to input an optical image corresponding to the X-ray transmitted through said slice to only one or a plurality of horizontal scanning lines in the imaging area of said solid-state pickup means; and
   said reading means comprises first means for vertically transferring, at the speed higher than the predetermined speed, data of horizontal scanning lines except for said one or a plurality of horizontal scanning lines, accumulating the transferred data in said horizontal transfer CCD, and outputting the accumulated data from said horizontal transfer CCD in the first operation mode and second means for vertically transferring the data of said one or a plurality of horizontal scanning lines at the predetermined speed, outputting the data of one horizontal scanning line from said horizontal transfer CCD when the data of the horizontal scanning line is vertically transferred by one line, and writing the output data in said memory means in the first operation mode.

5. The apparatus according to claim 4, in which said reading means comprises means for generating a first clock signal having a first frequency corresponding to the predetermined speed, means for generating a second clock signal having a second frequency corresponding to the speed higher than the predetermined speed, means for selecting one of said first and second clock signals in accordance with the position of said slice to supply the selected clock signal to said solid-state image pickup means as a vertical transfer clock signal in the first operation mode, means for supplying a horizontal transfer clock signal having a predetermined frequency to said solid-state image pickup means in synchronism with a selection operation of said selecting means, and means, connected between said solid-state image pickup means and said memory means, for turning on/off a signal path between said solid-state image pickup means and said memory means in synchronism with a selection operation of said selecting means.

6. An X-ray apparatus comprising:
   an X-ray source for emitting X-rays from a large number of directions onto a slice of an object;
   an image intensifier for converting the X-ray transmitted through said object into a light beam;

solid-state image pickup means for detecting the light beam output from said image intensifier to output image data;

means for reading only image data corresponding to said slice from said solid-state image pickup means at a first speed and outputting the image data which is read at the first speed and for reading image data corresponding to areas other than said slice from said solid-state image pickup means at a second speed higher than the first speed and discharging the image data which is read at the second speed; and means for obtaining a tomogram of said slice in accordance with the image data output from said reading means.

7. An X-ray apparatus comprising:

an X-ray source for emitting X-rays from a large number of directions onto a slice of an object;

an image intensifier for converting the X-ray transmitted through said object into a light beam;

solid-state image pickup means for detecting the light beam output from said image intensifier to output image data;

means for reading only image data corresponding to said slice form said solid-state image pickup means and for discharging image data corresponding to areas other than said slice from said solid-state image pickup means; and means for obtaining a tomogram of said slice in accordance with the image data read by said reading means;

wherein said X-ray source comprises means for changing a position and thickness of said slice onto which the X-ray is emitted;

said solid-state image pickup means comprises a CCD for outputting pixel data of a frame by repeating vertical and horizontal transfer of the pixel data; and said reading means comprises means for transferring only pixel data corresponding to said slice at normal speed, and transferring pixel data corresponding to a region except for said slice at a speed higher than the normal speed, and gate means, connected to an output terminal of said CCD, for causing the data transferred at the normal speed to pass, and interrupting passage of the data transferred at the speed higher than the normal speed.

8. The apparatus according to claim 7, in which said solid-state image pickup means comprises a plurality of vertical transfer CCDs, and a horizontal transfer CCD arranged at one end of the vertical transfer CCDs, only one or a plurality of predetermined horizontal scanning lines of which receive a light beam corresponding to the X-ray transmitted through said slice; and said reading means comprises first means for vertically transferring data of horizontal scanning lines except for said one or a plurality of predetermined horizontal scanning lines at the speed higher than the normal speed, accumulating the transferred data in a horizontal transfer CCD, and outputting the accumulated data from said horizontal transfer CCD and second means for vertically transferring the data of said one or a plurality of predetermined horizontal scanning lines at the normal speed.

9. The apparatus according to claim 8, in which said reading means comprises means for generating a first clock signal having a first frequency corresponding the normal speed, means for generating a second clock signal having a second frequency corresponding to the speed higher than the normal speed, means for selecting one of said first and second clock signals in accordance with the position and width of said slice to supply the selected signal to said solid-state image pickup means as a vertical transfer clock signal, and means for supplying a horizontal transfer clock signal having a predetermined frequency to said solid-state image pickup means in synchronism with a selection operation of said selecting means.

10. A method of obtaining a tomogram by using an X-ray fluoroscopic apparatus, comprising the steps of:

inserting an aperture between an X-ray source and an object to define a slice of said object;

emitting X-rays from a large number of directions onto said slice of said object through the aperture in order to make the X-ray transmitted through said slice incident on an image intensifier;

reading X-ray projection data from a solid-state image pickup element which picks up an optical image output from said image intensifier, data in only a region corresponding to said slice being read out at a first speed, and data in the remaining regions being read out at a second speed higher than the first speed and discharged;

storing the X-ray projection data which is read out at the first speed in a memory; and reconstructing a tomogram in accordance with the X-ray projection data stored in said memory.

11. A method of obtaining a tomogram by using an X-ray fluoroscopic apparatus, comprising the steps of:

inserting an aperture between an X-ray source and an object;

emitting X-rays from a large number of directions onto a slice of said object through the aperture in order to make the X-ray transmitted through said slice incident on an image intensifier;

reading X-ray projection data from a solid-state image pickup element which picks up an optical image output from said image intensifier, data in only a region corresponding to said slice being read out, data in the remaining regions being discharged;

storing the readout X-ray projection data in a memory; and reconstructing a tomogram in accordance with the X-ray projection data stored in said memory;

wherein said solid-state image pickup element comprises a plurality of vertical transfer CCDs, and a horizontal transfer CCD arranged at one end of the vertical transfer CCDs, and said slice corresponds to one or a plurality of horizontal scanning lines; and the step of reading X-ray projection data comprises the substeps of:

continuously and vertically transferring the pixel data immediately before data of the first horizontal scanning line in a region corresponding to said slice in one frame is written in said horizontal transfer CCD;

repeating an operation for vertically transferring the pixel data by one line after the data in said horizontal transfer CCD is horizontally transferred until data of the last horizontal scanning line in the region corresponding to said slice is output from said horizontal transfer CCD; and continuously and vertically transferring the remaining pixel data in said one frame.

* * * * *